(12) United States Patent
Nowak et al.

(10) Patent No.: US 10,174,022 B2
(45) Date of Patent: *Jan. 8, 2019

(54) 1-AMINO-TRIAZOLO(1,5-A)PYRIDINE-SUBSTITUTED UREA DERIVATIVE AND USES THEREOF

(71) Applicant: Kala Pharmaceuticals, Inc., Waltham, MA (US)

(72) Inventors: Pawel Wojciech Nowak, Waltham, MA (US); Minh Ngoc Nguyen, Waltham, MA (US); Elizabeth Enlow, Waltham, MA (US); Winston Zapanta Ong, Waltham, MA (US)

(73) Assignee: Kala Pharmaceuticals, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/534,448

(22) PCT Filed: Dec. 10, 2015

(86) PCT No.: PCT/US2015/065076
§ 371 (c)(1),
(2) Date: Jun. 8, 2017

(87) PCT Pub. No.: WO2016/094710
PCT Pub. Date: Jun. 16, 2016

(65) Prior Publication Data
US 2018/0057489 A1    Mar. 1, 2018

Related U.S. Application Data

(60) Provisional application No. 62/090,045, filed on Dec. 10, 2014.

(51) Int. Cl.
  *C07D 471/04* (2006.01)
  *C07D 401/04* (2006.01)
  *C07D 403/04* (2006.01)

(52) U.S. Cl.
  CPC ......... *C07D 471/04* (2013.01); *C07D 401/04* (2013.01); *C07D 403/04* (2013.01)

(58) Field of Classification Search
  CPC .................................................. C07D 471/04
  See application file for complete search history.

(56) References Cited

U.S. PATENT DOCUMENTS

| 7,276,491 B2 | 10/2007 | Wood et al. | |
| 9,212,145 B2 * | 12/2015 | Ong | A61K 9/146 |
| 9,580,421 B2 * | 2/2017 | Ong | A61K 9/146 |

FOREIGN PATENT DOCUMENTS

| WO | 2004/113304 A1 | 12/2004 | |
| WO | 2006/091801 A2 | 8/2006 | |
| WO | 2009/109071 A1 | 9/2009 | |
| WO | 2012/003141 A1 | 1/2012 | |
| WO | 2012/158810 A1 | 11/2012 | |
| WO | WO-2014201127 A2 * | 12/2014 | ............. A61K 9/146 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Dai et al., Discovery of N-(4-(3-Amino-1H-indazol-4-yl)phenyl)-N'-(2-fluoro-5-methylphenyl)urea (ABT-869), a 3-Aminoindazole-Based Orally Active Multitargeted Receptor Tyroisine Kinase Inhibitor, 50 J. Med. Chem. 1584-1597 (2007).
CAS Registry No. 1350231-66-1; STN Entry Date Dec. 7, 2011.
CAS Registry No. 1350196-55-2; STN Entry Date Dec. 7, 2011.
CAS Registry No. 1349824-73-2; STN Entry Date Dec. 6, 2011.
CAS Registry No. 1348459-21-1; STN Entry Date Dec. 4, 2011.
CAS Registry No. 1347883-53-7; STN Entry Date Dec. 4, 2011.
CAS Registry No. 1028316-86-0; STN Entry Date Jun. 15, 2008.
Wu, X. et al., "Molecular docking and 3D-QSAR study on 4-(1H-indazol-4-yl)phenylamino and aminopyrazolopyridine urea derivatives as kinase insert domain receptor (KDR) inhibitors", Journal of Molecular Modeling, 2012, vol. 18, No. 3, pp. 1207-1218.
CAS Registry No. 1349474-31-2; STN Entry Date Dec. 6, 2011.
Database WPI: Week 200905; AN2009-A292379 & CN 101 239 978 A (Univ Southern Medical) Aug. 13, 2008.

* cited by examiner

*Primary Examiner* — David K O'Dell
(74) *Attorney, Agent, or Firm* — K&L Gates LLP; Louis C. Cullman; Michelle Glasky Bergman

(57) ABSTRACT

Provided herein is a compound, 1-(4-(3-amino-[1,2,3]triazolo[1,5-a]pyridin-4-yl)phenyl)-3-(3-chlorophenyl)urea, pharmaceutical compositions thereof, and crystal forms thereof. Also provided are particles (e.g., nanoparticles) comprising the compound, and pharmaceutical compositions thereof, that are mucus penetrating. Also provided herein are methods and kits for using the compound, and pharmaceutical compositions thereof, for treating and/or preventing diseases associated with abnormal or pathological angiogenesis and/or aberrant signaling of a growth factor (e.g., vascular endothelial growth factor (VEGF)), such as proliferative diseases (e.g., cancers, benign neoplasms, inflammatory diseases, autoimmune diseases) and ocular diseases (e.g., macular degeneration, glaucoma, diabetic retinopathy, retinoblastoma, edema, uveitis, dry eye, blepharitis, and post-surgical inflammation) in a subject in need thereof.

9 Claims, 4 Drawing Sheets

1-AMINO-TRIAZOLO(1,5-A)PYRIDINE-SUBSTITUTED UREA DERIVATIVE AND USES THEREOF

BACKGROUND

Growth factors play an important role in angiogenesis, lymphangiogenesis, and vasculogenesis, and they regulate angiogenesis in a variety of processes. Undesirable or pathological angiogenesis is associated with diseases including diabetic retinopathy, psoriasis, cancer, rheumatoid arthritis, atheroma, Kaposi's sarcoma, and hemangioma. Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively.

Therefore, there is a need for new therapeutic compounds for the treatment of diseases associated with the aberrant signaling of growth factors and diseases associated with angiogenesis, such as cancer, macular degeneration, and diabetic retinopathy.

SUMMARY

Disclosed herein are urea derivatives such as 1-(4-(3-amino-[1,2,3]triazolo[1,5-a]pyridin-4-yl)phenyl)-3-(3-chlorophenyl)urea, which is shown in Formula (I) below,

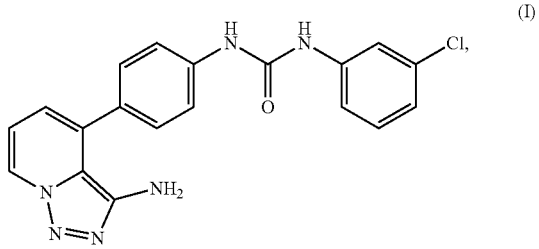 [SMILES: Nc1nnn2cccc(-c3ccc(NC(=O)Nc4cccc(Cl)c4)cc3)c12]

and pharmaceutical compositions thereof, and methods useful in treating and/or preventing diseases associated with abnormal angiogenesis and/or aberrant signaling of a growth factor (e.g., vascular endothelial growth factor (VEGF)). Diseases that may be treated and/or prevented by the disclosed compounds, pharmaceutical compositions, kits, uses, and methods include proliferative diseases (e.g., cancers, benign neoplasms, inflammatory diseases, autoimmune diseases) and ocular diseases (e.g., macular degeneration, glaucoma, diabetic retinopathy, retinoblastoma, edema, uveitis, dry eye, blepharitis, and post-surgical inflammation).

In one aspect, disclosed herein is a compound of Formula (I):

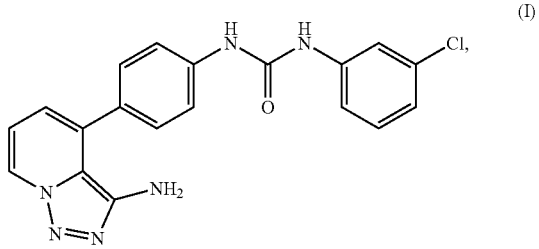 [SMILES: Nc1nnn2cccc(-c3ccc(NC(=O)Nc4cccc(Cl)c4)cc3)c12]

and pharmaceutically acceptable salts, solvates, hydrates, polymorphs, co-crystals, tautomers, stereoisomers, and prodrugs thereof.

In another aspect, disclosed herein is a crystal form of

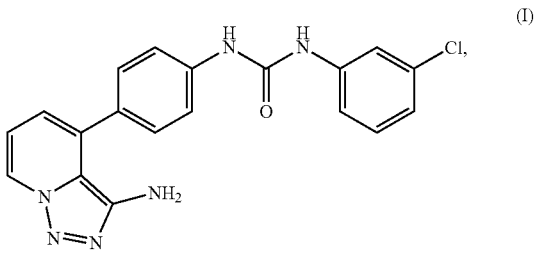 [SMILES: Nc1nnn2cccc(-c3ccc(NC(=O)Nc4cccc(Cl)c4)cc3)c12]

wherein the crystal form has an X-ray powder diffraction (XRPD) pattern with peaks at about 10.5 (e.g., 10.54), about 14.4 (e.g., 14.35), about 19.3 (e.g., 19.26), about 21.7 (e.g., 21.67), and about 24.7 (e.g., 24.72) degrees 2θ.

Also disclosed herein are pharmaceutical compositions comprising 1-(4-(3-amino-[1,2,3]triazolo[1,5-a]pyridin-4-yl)phenyl)-3-(3-chlorophenyl)urea or a compound of Formula (I), or the crystal form, and a pharmaceutically acceptable excipient or carrier. In certain embodiments, the pharmaceutical compositions described herein include an effective amount of the compound disclosed herein. The pharmaceutical composition may be useful for treating proliferative diseases (e.g., cancers, benign neoplasms, inflammatory diseases, autoimmune diseases) and/or ocular diseases (e.g., macular degeneration, glaucoma, diabetic retinopathy, retinoblastoma, edema, uveitis, dry eye, blepharitis, and post-surgical inflammation) in a subject in need thereof. The pharmaceutical composition may also be useful for inhibiting abnormal angiogenesis and/or aberrant signaling of a growth factor in a subject or cell.

In some embodiments, the compound of Formula (I), 1-(4-(3-amino-[1,2,3]triazolo[1,5-a]pyridin-4-yl)phenyl)-3-(3-chlorophenyl)urea may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). In one aspect the compound of Formula (I), 1-(4-(3-amino-[1,2,3]triazolo[1,5-a]pyridin-4-yl)phenyl)-3-(3-chlorophenyl)urea, is formulated into mucus penetrating particles or mucus penetrating crystals (collectively, MPPs) suitable for administration (e.g., topical or inhalation) to tissues of the subject having mucus (e.g., eye, respiratory tract, gastrointestinal tract, genito-urinary tract).

In another aspect, disclosed herein are particles comprising 1-(4-(3-amino-[1,2,3]triazolo[1,5-a]pyridin-4-yl)phenyl)-3-(3-chlorophenyl)urea. In certain embodiments, the particles are mucus penetrating. The particles may include a coating surrounding a core. The core may comprise primarily the compound of Formula (I), or the core may be a polymeric core with the compound encapsulated in the polymer. In certain embodiments, the particles are nanoparticles (e.g., particles having an average diameter of at least about 10 nm and less than about 1 μm). The particles may be useful in delivering the compound of Formula (I) to a subject. In certain embodiments, the particles are capable of delivering the compound in or through mucus of a subject.

Another aspects relate to pharmaceutical compositions comprising a compound of Formula (I), 1-(4-(3-amino-[1,2,3]triazolo[1,5-a]pyridin-4-yl)phenyl)-3-(3-chlorophenyl)

urea, and/or a plurality of particles. In certain embodiments, the pharmaceutical compositions are useful in delivering the compound of Formula (I) to a subject.

In other aspects, disclosed herein are pharmaceutical compositions comprising a plurality of particles comprising (i) a core comprising 1-(4-(3-amino-[1,2,3]triazolo[1,5-a]pyridin-4-yl)phenyl)-3-(3-chlorophenyl)urea, or a pharmaceutically acceptable salt thereof, and (ii) a coating of a surface altering agent surrounding the core, wherein the surface altering agent is present on the outer surface of the core at a density of at least 0.01 surface altering agent per $nm^2$, and optionally, at least one pharmaceutically acceptable excipient or carrier. In some embodiments, the surface altering agent is a triblock copolymer of the structure (hydrophilic block)-(hydrophobic block)-(hydrophilic block). In some aspects, the triblock copolymer is a PLURONIC® or a poloxamer, a poly(vinyl alcohol) that is less than 95% hydrolyzed, or a polysorbate.

In certain embodiments, the compound, particle, or pharmaceutical composition is formulated to be mucus penetrating.

Other aspects disclosed herein relate to methods of treating and/or preventing a disease associated with abnormal angiogenesis in a subject in need thereof.

Other aspects disclosed herein relate to methods of treating and/or preventing a disease associated with aberrant signaling of a growth factor signaling pathway in a subject in need thereof.

In other aspects, disclosed herein are methods of inhibiting angiogenesis in a subject in need thereof.

In other aspects, provided herein are methods of inhibiting aberrant signaling of a growth factor signaling pathway in a subject or cell. In certain embodiments, the growth factor is associated with angiogenesis. In certain embodiments, the growth factor is VEGF.

The methods disclosed herein include administering to the subject an effective amount of a compound of Formula (I) or pharmaceutical composition disclosed herein. In certain embodiments, the effective amount is a therapeutically effective amount. In certain embodiments, the effective amount is a prophylactically effective amount.

In yet other aspects, provided herein are the compound of Formula (I) and pharmaceutical compositions for use in the treatment and/or prevention of a disease associated with abnormal angiogenesis and/or associated with aberrant signaling of a growth factor signaling pathway in a subject in need thereof.

The present application refers to various issued patent, published patent applications, journal articles, and other publications, all of which are incorporated herein by reference.

The details of one or more embodiments are set forth herein. Other features, objects, and advantages will be apparent from the Detailed Description, the Figures, the Examples, and the Claims.

DETAILED DESCRIPTION

Definitions

Figure 1:
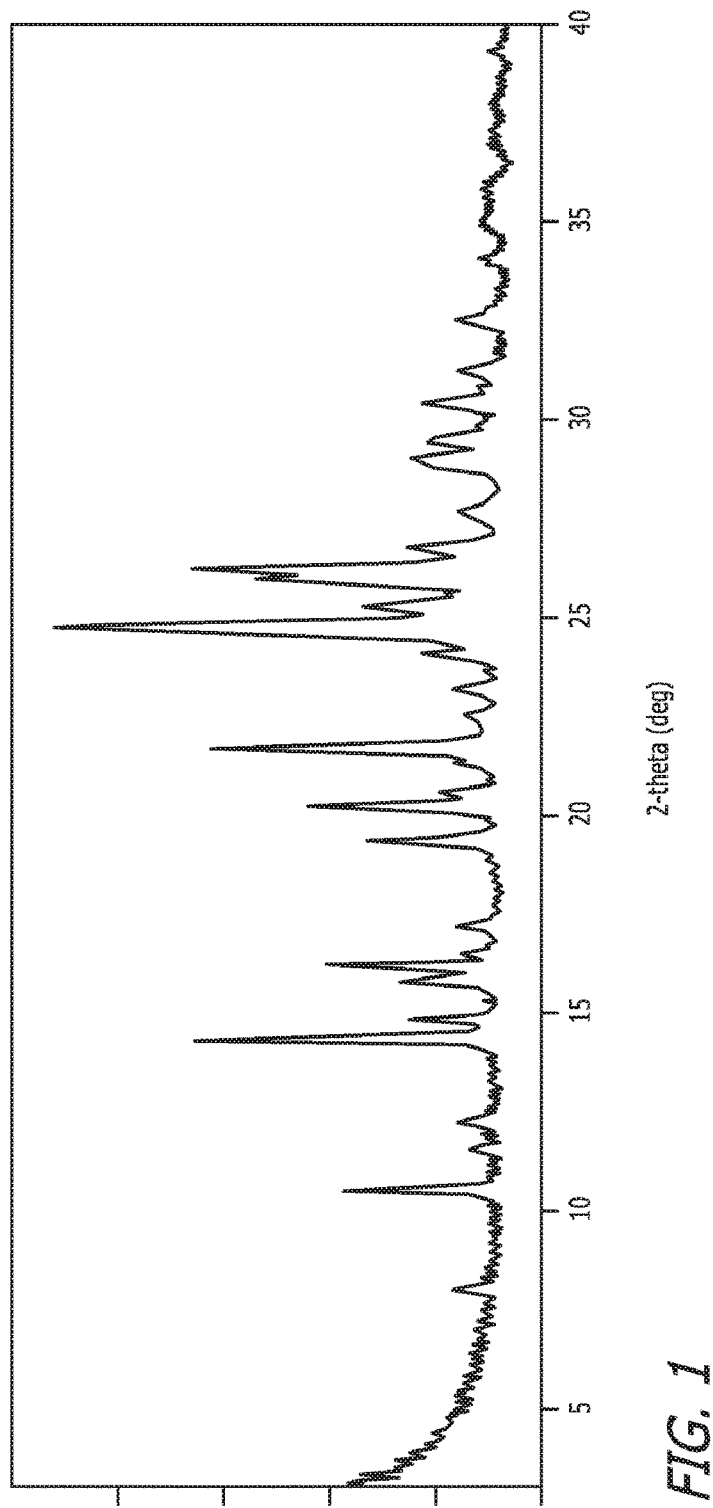
FIG. 1 depicts the X-ray powder diffraction (XRPD) pattern of crystal form I.

The following definitions are more general terms used throughout the present application.

As used herein, the term "pharmaceutically acceptable salt" refers to those salts which are, within the scope of sound medical judgment, suitable for use in contact with the tissues of humans and lower animals. Examples of pharmaceutically salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "prodrugs" refer to compounds, including derivatives of the compounds described herein, which have cleavable groups which are removed in vivo to leave a parent compound that is pharmaceutically. Such examples include, but are not limited to, choline ester derivatives and the like, N-alkylmorpholine esters and the like. Other derivatives of the compounds have activity in both their acid and acid derivative forms, but in the acid sensitive form often offer advantages of solubility, tissue compatibility, or delayed release in the mammalian organism. Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "administer," "administering," or "administration," as used herein, refers to implanting, absorbing, ingesting, injecting, inhaling, or otherwise introducing the compound of Formula (I), or a pharmaceutical composition thereof, in or on a subject.

As used herein, the terms "treatment," "treat," and "treating" refer to preventing, reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a "therapeutically effective amount" of a compound or composition is the amount needed to inhibit angiogenesis in a subject.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "growth factor" refers to a naturally occurring substance (e.g., a protein or a steroid hormone) capable of stimulating cellular growth, proliferation, and cellular differentiation. Growth factors may act as signaling molecules between cells and/or promote cell differentiation and maturation.

As used herein, the term "vascular endothelial growth factor" or "VEGF" refers to a signal protein produced by cells that stimulate vasculogenesis and angiogenesis. VEGFs are a sub-family of growth factors, i.e., the platelet-derived growth factor family of cysteine-knot growth factors. VEGFs are important signaling proteins involved in both vasculogenesis and angiogenesis. VEGFs' normal function is to create new blood vessels during embryonic development, new blood vessels after injury, muscle following exercise, and new vessels (collateral circulation) to bypass blocked vessels. When VEGF is overexpressed, it can contribute to a range of diseases, such as proliferative diseases (e.g., cancer) and vascular diseases in the retina of the eye and other parts of the body. VEGFs include a number of proteins from two families that result from alternate splicing of mRNA from a single, 8-exon, VEGF gene. Examples of VEGFs include, but are not limited to, VEGF-related proteins such as placental growth factor (PGF), VEGF-A, VEGF-B, VEGF-C, VEGF-D, VEGF-E, and VEGF-F. The term "VEGF" also encompasses VEGF receptors (VEGFRs), such as VEGFR-1, VEGFR-2 and VEGFR-3. A VEGFR may be membrane-bound (mbVEGFR) or soluble (sVEGFR).

A "proliferative disease" refers to a disease that occurs due to abnormal growth or extension by the multiplication of cells. A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

As used herein, the term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm.

As used herein, the term "inflammatory disease" or "inflammation" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Examples of inflammatory diseases include, without limitation, autoimmune disorders, systemic lupus erythematosus, psoriasis, cystic fibrosis, rheumatoid arthritis, inflammatory arthritis, Sjogren's syndrome, inflammatory bowel disease, Crohn's disease, ulcerative colitis, pneumonia, respiratory tract inflammation, adult respiratory distress syndrome (ARDS), asthma, allograft rejection, and vaginitis. Ocular inflammatory diseases include, but are not limited to, allergy of the eye, uveitis (e.g., anterior uveitis, intermediate uveitis, and posterior uveitis), conjunctivitis, panuveitis, cyclitis, scleritis, episcleritis, optic neuritis, retrobulbar optic neuritis, keratitis (e.g., immune keratitis and infectious keratitis), blepharitis, corneal ulcer, conjunctival ulcer and symptoms caused by them, ocular inflammatory diseases caused by ocular disorders, ocular inflammatory diseases caused by a physical injury, post-surgical inflammation, and dry eye (e.g., dry eye syndrome).

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney).

The term "ocular disease" or "ocular disorder" refers to any eye disease and/or disorder. For example, ocular diseases can be disorders of the eyelid, lacrimal system and orbit, disorders of conjunctiva, disorders of sciera, cornea, iris and ciliary body, disorders of choroid and retina, glaucoma, disorders of optic nerve and visual pathways, occulary inflammatory diseases, or disorders of ocular muscles. Additionally, ocular disease can also refer to discomfort following injury, surgery, or laser treatment. Diseases and disorders of the eye include, but are not limited to, macular degeneration, dry eye syndrome, uveitis, allergic conjunctivitis, glaucoma, and ocular rosacea. Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals The term "age-related macular degeneration" or "AMD" is an ocular disease which usually affects older adults and results in a loss of vision in the center of the visual field (the macula) because of damage to the retina. It occurs in "dry" and "wet" forms. It is a major cause of blindness and visual impairment in older adults (>50 years). Macular degeneration can make it difficult or impossible to read or recognize faces, although enough peripheral vision remains to allow other activities of daily life. In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached. AMD can be treated with laser coagulation, and with medication that stops and sometimes reverses the growth of blood vessels. AMD begins with characteristic yellow deposits (drusen) in the macula, between the retinal pigment epithelium and the underlying choroid. Most patients with these early changes (referred to as age-related maculopathy) have good vision. Patients with drusen can go on to develop advanced AMD. The risk is considerably higher when the drusen are large and numerous and associated with disturbance in the pigmented cell layer under the macula.

The term "macular edema" refers to the ocular diseases cystoid macular edema (CME) or diabetic macular edema (DME). CME is an ocular disease that affects the central retina or macula of the eye. When this condition is present, multiple cyst-like (cystoid) areas of fluid appear in the macula and cause retinal swelling or edema. CME may accompany a variety of diseases such as retinal vein occlusion, uveitis, and/or diabetes. CME commonly occurs after cataract surgery. DME occurs when blood vessels in the retina of patients with diabetes begin to leak into the macula, the part of the eye responsible for detailed central vision. These leaks cause the macula to thicken and swell, progressively distorting acute vision. While the swelling may not lead to blindness, the effect can cause a severe loss in central vision.

The term "glaucoma" refers to an ocular disease in which the optic nerve is damaged in a characteristic pattern. This can permanently damage vision in the affected eye and lead to blindness if left untreated. It is normally associated with increased fluid pressure in the eye (aqueous humor). The term ocular hypertension is used for patients with consistently raised intraocular pressure (IOP) without any associated optic nerve damage. Conversely, the term normal tension or low tension glaucoma is used for those with optic nerve damage and associated visual field loss but normal or low IOP. The nerve damage involves loss of retinal ganglion cells in a characteristic patter. There are many different subtypes of glaucoma, but they can all be considered to be a type of optic neuropathy. Raised intraocular pressure (e.g., above 21 mmHg or 2.8 kPa) is the most important and only modifiable risk factor for glaucoma, though some may have high eye pressure for years and never develop damage, while others can develop nerve damage at a relatively low pressure. Untreated glaucoma can lead to permanent damage of the optic nerve and resultant visual field loss, which over time can progress to blindness.

The term "uveitis" refers to an inflammatory disease of the uvea, the vascular layer of the eye sandwiched between the retina and the sclera (white of the eye). The uvea extends toward the front of the eye and consists of the iris, choroid layer and ciliary body. Uveitis includes anterior uveitis, intermediate uveitis, and posterior uveitis. A common type of uveitis is an inflammation of the iris called iritis (anterior uveitis). Uveitis may also occur at the posterior segment of the eye (e.g., at the choroid). Inflammation of the uvea can be recurring and can cause serious problems such as blindness if left untreated, and accounts for 10% of blindness globally. Early diagnosis and treatment are important to prevent the complications of uveitis.

The term "dry eye" or "dry eyes" refers to an ocular disease in which there are insufficient tears to lubricate and nourish the eye. Tears are necessary for maintaining the health of the front surface of the eye and for providing clear vision. Patients with dry eyes either do not produce enough tears or have a poor quality of tears. Dry eye is a common and often chronic problem, particularly in older adults. With each blink of the eyelids, tears are spread across the front surface of the eye, known as the cornea. Tears provide lubrication, reduce the risk of eye infection, wash away foreign matter in the eye, and keep the surface of the eyes smooth and clear. When the normal amount of tear production decreases or tears evaporate too quickly from the eyes, symptoms of dry eye can develop. The most common form of dry eyes is due to an inadequate amount of the water layer of tears. This condition, called keratoconjunctivitis sicca (KCS), is also referred to as "dry eye syndrome." A non-limiting example of dry eye syndrome is Sjögren's syndrome.

The term "diabetic retinopathy" refers to retinopathy (i.e., a disease of the retina) caused by complications of diabetes, which can eventually lead to blindness. Diabetic retinopathy may cause no symptoms, mild vision problems, or even blindness. Diabetic retinopathy is the result of microvascular retinal changes. Hyperglycemia-induced intramural pericyte death and thickening of the basement membrane lead to incompetence of the vascular walls. These damages change the formation of the blood-retinal barrier and also make the retinal blood vessels become more permeable. Small blood vessels, such as those in the eye, are especially vulnerable to poor control over blood sugar. An overaccumulation of glucose and/or fructose damages the tiny blood vessels in the retina. During the initial stage, called "nonproliferative diabetic retinopathy" (NPDR), most patients do not notice any change in their vision. Early changes that are reversible and do not threaten central vision are sometimes termed simplex retinopathy or background retinopathy. As the disease progresses, severe nonproliferative diabetic retinopathy enters an advanced, "proliferative diabetic retinopathy" (PDR) stage when blood vessels proliferate. The lack of oxygen in the retina causes fragile, new, blood vessels to grow along the retina and in the clear, gel-like vitreous humor that fills the inside of the eye, which may result in bleeding, cloudy vision, retina damage, or tractional retinal detachment.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals (e.g., crystalline forms of compounds or active pharmaceutical agent), aggregates, composites, pulverized, milled, or otherwise disrupted matrices, and cross-linked protein or polysaccharide particles. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension in a nanometer range, such as less than about 1 micrometer and at least about 1 nanometer, where the characteristic dimension of the particle is the smallest cross-sectional dimension of the particle. A crystalline nanoparticle is referred to as a "nanocrystal."

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" to materials that are composed of substantially a single crystallite of substantially the same size and orientation.

"Nanocrystal" is a nanostructure that is substantially monocrystalline. A nanocrystal thus has at least one region or characteristic dimension with a dimension in the nanometer range, such as less than about 1000 nm, e.g., less than about 300 nm, less than about 200 nm, less than about 100 nm, or less than about 50 nm. Typically, the region or characteristic dimension will be along the smallest axis of the structure. Optionally, a nanocrystal can comprise one or more surface ligands (e.g., surfactants). The nanocrystal is optionally substantially single crystal in structure (a "single crystal nanostructure" or a "monocrystalline nanostructure"). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be.

The term "polycrystalline" refers to materials that are composed of many crystallites of varying size and orientation. When used with respect to nanostructures, the term "polycrystalline" refers to a crystalline nanostructure that is not monocrystalline.

As used herein, the terms "pharmaceutical composition" and "formulation" are used interchangeably.

As used herein, the terms "pharmaceutical agent" and "drug" are used interchangeably.

DETAILED DESCRIPTION OF CERTAIN EMBODIMENTS

The present disclosure provides a compound having the formula

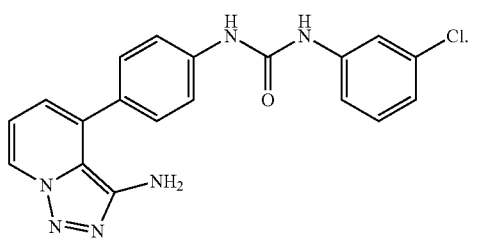

(I)

or 1-(4-(3-amino-[1,2,3]triazolo[1,5-a]pyridin-4-yl)phenyl)-3-(3-chlorophenyl)urea, and pharmaceutically acceptable salts and prodrugs thereof.

Unless otherwise indicated, reference to a compound, such as a compound of Formula I, by structure or name includes alternate solid forms such as solvates, hydrates, polymorphs, co-crystals; tautomers; and stereoisomers, such as diastereomers and enantiomers, including diastereomeric mixtures (both equal mixtures and mixtures enriched with one or more diastereomers) and enantiomeric mixtures (both racemic mixtures and mixtures having an enantiomeric excess).

In one embodiment, the compound of Formula (I) is formulated into mucus-penetrating particles or mucus-penetrating nanocrystals (collectively, MPPs) suitable for administration (e.g., topical or inhalation) to tissues of the subject having mucus (e.g., eye, respiratory tract, gastrointestinal tract, genito-urinary tract).

In another aspect, the present disclosure provides particles comprising 1-(4-(3-amino-[1,2,3]triazolo[1,5-a]pyridin-4-yl)phenyl)-3-(3-chlorophenyl)urea. In certain embodiments, the particles are nanoparticles. In one aspect, the nanoparticles are mucus penetrating. The particles may include a coating surrounding a core. The core may comprise primarily the compound of Formula (I), or the core may be a polymeric core with the compound encapsulated in the polymer. In certain embodiments, the particles are nanoparticles (e.g., particles having an average diameter of at least about 10 nm and less than about 1 μm). The particles may be useful in delivering the compound of Formula (I) to a subject. In certain embodiments, the particles are capable of delivering the compound in or through mucus of a subject.

In some embodiments, the compound of Formula (I) described herein may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). For effective drug delivery, compound or particles that are immobilized in the mucus are quickly eliminated by mucus clearance mechanisms; therefore, they are not able to effectively deliver the intended therapeutic effect. In these tissues, for the compound to effective, it must quickly penetrate the mucus and/or avoid mucus clearance mechanisms. Accordingly, modifying mucoadhesive compounds or particles containing compounds with a coating to reduce the mucoadhesiveness, and decreasing the size of the particles of compound may allow for efficient delivery and therapeutic effect.

In one aspect, a compound of Formula (I), or 1-(4-(3-amino-[1,2,3]triazolo[1,5-a]pyridin-4-yl)phenyl)-3-(3-chlorophenyl)urea, is formulated into mucus-penetrating particles or mucus-penetrating nanocrystals (collectively, MPPs) suitable for administration (e.g., topical or inhalation) to tissues of the subject having mucus (e.g., eye, respiratory tract, gastrointestinal tract, genito-urinary tract).

1-(4-(3-amino-[1,2,3]triazolo[1,5-a]pyridin-4-yl)phenyl)-3-(3-chlorophenyl)urea, or mucus-penetrating particles or mucus-penetrating nanocrystals thereof, may be suitable for being processed into mucus-penetrating pharmaceutical compositions (e.g., particles or crystals). In certain embodiments, the compound is suitable for milling (e.g., nanomilling). In certain embodiments, the compound is suitable for precipitation (e.g., microprecipitation, nanoprecipitation, crystallization, or controlled crystallization). In certain embodiments, the compound is suitable for emulsification. In certain embodiments, the compound is suitable for freeze-drying.

The present disclosure provides pharmaceutical compositions comprising a compound of Formula (I), or a pharmaceutically acceptable salt, solvate, hydrate, polymorph, co-crystal, tautomer, stereoisomer, or prodrug thereof, and a pharmaceutically acceptable excipient or carrier. In certain embodiments, the pharmaceutical composition comprises a compound of Formula (I), or a pharmaceutically acceptable salt thereof, and a pharmaceutically acceptable excipient or carrier.

In another aspect, the present disclosure provides a pharmaceutical composition comprising 1-(4-(3-amino-[1,2,3]triazolo[1,5-a]pyridin-4-yl)phenyl)-3-(3-chlorophenyl)urea, or a pharmaceutically acceptable salt, solvate, hydrate, polymorph, co-crystal, tautomer, stereoisomer, or prodrug thereof, and a pharmaceutically acceptable excipient or carrier. In certain embodiments, the pharmaceutical composition comprises 1-(4-(3-amino-[1,2,3]triazolo[1,5-a]pyridin-4-yl)phenyl)-3-(3-chlorophenyl)urea, or a pharmaceutically acceptable salt thereof, and a pharmaceutically acceptable excipient or carrier.

In certain embodiments, the compound of Formula (I), or 1-(4-(3-amino-[1,2,3]triazolo[1,5-a]pyridin-4-yl)phenyl)-3-(3-chlorophenyl)urea, is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease. In certain embodiments, the effective amount is an amount effective for treating and/or preventing a disease associated with aberrant signaling of a growth factor. In certain embodiments, the effective amount is an amount effective for treating a disease associated with aberrant signaling of a growth factor. In certain embodiments, the effective amount is an amount effective for treating and/or preventing a disease associated with aberrant signaling of vascular endothelial growth factor (VEGF). In certain embodiments, the effective amount is an amount effective for treating a disease associated with aberrant signaling of vascular endothelial growth factor (VEGF). In certain embodiments, the effective amount is an amount effective for treating and/or preventing a disease associated with abnormal angiogenesis, such as cancer, benign neoplasm, atherosclerosis, hypertension, inflammatory disease, rheumatoid arthritis, macular degeneration, an ocular neovascular disease, choroidal neovascularization, retinal neovascularization, neovascular glaucoma, and diabetic retinopathy. In certain embodiments, the effective amount is an amount effective to treat cancer (e.g., an ocular cancer). In certain embodiments, the effective amount is an amount effective to treat macular degeneration.

An effective amount of a compound may vary from about 0.001 mg/kg to about 1000 mg/kg in one or more close administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An effective amount of a compound disclosed herein may inhibit abnormal angiogenesis and/or aberrant signaling of a growth factor by at least about 10%, at least about 20%, at least about 30%, at least about 40%, at least about 50%, at least about 60%, at least about 70%, at least about 80%, or at least about 90%. An effective amount of a compound disclosed herein may inhibit abnormal angiogenesis and/or aberrant signaling of a growth factor by less than about 90%, less than about 80%, less than about 70%, less than about 60%, less than about 50%, less than about 40%, less than about 30%, less than about 20%, or less than about 10%. Combinations of the ranges described herein (e.g., at least 20% and less than 50%) are also within the scope of the present disclosure. In certain embodiments, an effective amount of a compound disclosed herein inhibits abnormal angiogenesis and/or aberrant signaling of a growth factor by a percentage or a range of percentage described herein, compared to normal angiogenesis and/or signaling.

Pharmaceutical compositions described herein can be prepared by any method known in the art of pharmacology. In general, such preparatory methods include the steps of bringing the compound of Formula (I) described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient, a compound of Formula (I) or 1-(4-(3-amino-[1,2,3]triazolo[1,5-a]pyridin-4-yl)phenyl)-3-(3-chlorophenyl)urea, is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

A compound of Formula (I), or 1-(4-(3-amino-[1,2,3]triazolo[1,5-a]pyridin-4-yl)phenyl)-3-(3-chlorophenyl)urea, and pharmaceutical compositions thereof provided herein, can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by solutions, suspensions, drops, powders, ointments, gels, and/or creams), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, topical administration, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition disclosed herein is suitable for topical administration to the eye of a subject.

In one aspect, the pharmaceutical compositions are suitable for topical administration. In another aspect, the pharmaceutical compositions are suitable for injection. In one embodiment, the pharmaceutical compositions comprising a compound of Formula (I) are suitable for delivery to the eye. In another aspect, pharmaceutical compositions comprising a compound of Formula (I) are suitable for oral administration. In yet another aspect, the pharmaceutical compositions comprising a compound of Formula (I) are suitable for inhalation.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers, and mixtures thereof. Besides inert diluents, the oral compositions can include adjuvants such as wetting agents, emulsifying and suspending agents, sweetening, flavoring, and perfuming agents.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent. The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

Compositions for rectal or vaginal administration are typically suppositories that can be prepared by mixing an active ingredient as described herein with suitable nonirritating excipients or carriers such as cocoa butter, polyethylene glycol, or a suppository wax that are solid at ambient temperature but liquid at body temperature and therefore melt in the rectum or vaginal cavity and release the active ingredient.

Solid dosage forms for oral administration include capsules, gelatin capsules, tablets, pills, powders, and granules. In such solid dosage forms, the active ingredient (e.g., a compound of Formula (I)) is mixed with at least one inert, pharmaceutically acceptable excipient or carrier known in the art, including without limitation fillers or extenders, binders, humectants, disintegrating agents, solution retarding agents, absorption accelerators, wetting agents, absorbents, and lubricants, and mixtures thereof. In the case of capsules, tablets, and pills, the dosage form may include a buffering agent.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art.

Dosage forms for topical and/or transdermal administration of a compound of Formula (I) may include solutions, suspensions, ointments, pastes, creams, lotions, gels, powders, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662, all of which are incorporated by reference herein for all they teach regarding intradermal pharmaceutical delivery. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537, all of which are incorporated by reference herein for all they teach regarding jet injection devices. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as solutions, suspensions, liniments, lotions, oil-in-water and/or water-in-oil emulsions such as creams, ointments, and/or pastes. Topically administrable formulations may, for example, comprise from about 1% to about 10% (w/w) of pharmaceutical agent (e.g., a compound of Formula (I)), although the concentration of the pharmaceutical agent can be as high as the solubility limit of the pharmaceutical agent in the solvent. Formulations for topical administration may further comprise one or more of the additional ingredients described herein. In one embodiment, pharmaceutical compositions suitable for topical administration are solutions or suspensions. In another embodiment, the solution or suspension is in the form of eye drops.

A pharmaceutical composition can be prepared, packaged, and/or sold in a formulation suitable for pulmonary administration via the buccal cavity. Such a formulation may comprise dry particles that comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition disclosed herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein.

A pharmaceutical composition disclosed herein can be prepared, packaged, and/or sold in a formulation for ophthalmic administration, such as solutions, suspensions, ointments, or gels. Such formulations may, for example, be in the form of eye drops including, for example, a 0.1/1.0% (w/w) solution and/or suspension of the active ingredient (e.g., a compound of Formula (I)) in an aqueous or oily liquid carrier or excipient. Such drops may further comprise buffering agents, salts, and/or one or more other of the additional ingredients described herein. Other ophthalmically-administrable formulations that are useful include those which comprise the active ingredient in microcrystalline form and/or in a liposomal preparation. Eye drops are also contemplated as being within the scope of this disclosure.

Although the descriptions of pharmaceutical compositions provided herein are principally directed to pharmaceutical compositions that are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

A compound of Formula (I) provided herein may be formulated in dosage unit form for ease of administration and uniformity of dosage. It will be understood, however, that the total daily usage of the compositions disclosed herein will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound of Formula (I), or 1-(4-(3-amino-[1,2,3]triazolo[1,5-a]pyridin-4-yl)phenyl)-3-(3-chlorophenyl)urea, required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound of Formula (I) for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound of Formula (I) described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that close ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In certain embodiments, a compound of Formula (I), or 1-(4-(3-amino-[1,2,3]triazolo[1,5-a]pyridin-4-yl)phenyl)-3-(3-chlorophenyl)urea, pharmaceutical compositions thereof, and methods disclosed herein are useful for applications in the eye, such as treating and/or preventing an ocular disease (e.g., macular degeneration, dry eye syndrome, diabetic macular edema, cystoid macular edema, uveitis, allergic conjunctivitis, glaucoma, and ocular rosacea). In certain embodiments, the pharmaceutical compositions disclosed herein can be topically administered to the eye of a subject. Topical pharmaceutical compositions administered to the eye are advantageous over pharmaceutical compositions that are administered to the eye by injection or orally.

In certain embodiments, a compound of Formula (I), or 1-(4-(3-amino-[1,2,3]triazolo[1,5-a]pyridin-4-yl)phenyl)-3-(3-chlorophenyl)urea, is formulated as a mucus-penetrating particles. Methods for preparing mucus-penetrating particles have been described in, for example, U.S. Patent Publication Nos. 2008/0166414, 2010/0215580, 2013/0164343, 2013/0236556, 2013/0316001, 2013/0316006, 2013/0316009, and 2013/0323179, each of which is herein incorporated by reference for all they teach regarding mucus penetrating particles.

In one embodiment, disclosed herein are pharmaceutical compositions comprising a compound of Formula (I), or 1-(4-(3-amino-[1,2,3]triazolo[1,5-a]pyridin-4-yl)phenyl)-3-(3-chlorophenyl)urea, wherein said pharmaceutical composition comprises mucus-penetrating particles of a compound of Formula (I), or 1-(4-(3-amino-[1,2,3]triazolo[1,5-a]pyridin-4-yl)phenyl)-3-(3-chlorophenyl)urea, and a pharmaceutically acceptable excipient or carrier, and wherein said mucus-penetrating particles have reduced inflammation upon administration to a subject.

The compound of Formula (I), or 1-(4-(3-amino-[1,2,3]triazolo[1,5-a]pyridin-4-yl)phenyl)-3-(3-chlorophenyl)urea, is a potent inhibitor of VEGF receptor-2 (VEGFR2) and platelet-derived growth factor receptor-$\beta$ (PDGFR-$\beta$).

A compound of Formula (I) may be used in treating and/or preventing a disease (e.g., a disease associated with abnormal angiogenesis and/or aberrant signaling of a growth factor signaling pathway (e.g., VEGF)) in a subject in need thereof. The compounds disclosed herein may also be used in inhibiting abnormal angiogenesis and/or aberrant signaling of a growth factor pathway in a subject and/or cell.

A range of diseases may result when the body of a subject loses control over angiogenesis, i.e., new blood vessels grow abnormally (i.e., excessively or insufficiently) or grow as a result of a tumor. Excessive angiogenesis is often observed in subjects with diseases such as proliferative diseases (e.g., cancers, benign neoplasms, inflammatory diseases, autoimmune diseases) and ocular diseases, especially with cancer, diabetic retinopathy, macular degeneration, rheumatoid arthritis, and psoriasis. In these diseases, new blood vessels feed abnormal tissues and/or destroy normal tissues. Excessive angiogenesis may occur when there are abnormal amounts of angiogenic growth factors present, overwhelming the effects of natural angiogenesis inhibitors. Therefore, inhibiting new blood vessel growth may be useful to treat diseases associated with excessive angiogenesis. Insufficient angiogenesis is typically observed in subjects with a disease such as coronary artery disease, stroke, or chronic wounds. In these diseases, blood vessel growth is inadequate, and circulation is not properly restored, which may lead to tissue death.

VEGFs have been found to play a major role in angiogenesis, for example, by increasing the number of capillaries in a given network. In vitro studies have demonstrated that bovine capillary endothelial cells proliferated and showed signs of tube structures upon stimulation with VEGF. Upregulation of VEGF is a major component of the physiological response to exercise and its role in angiogenesis is suspected to be a possible treatment in vascular injuries. In vitro studies have showed that VEGFs are a potent stimulator of angiogenesis because, among other things, in the presence of this growth factor, plated endothelial cells will proliferate and migrate, eventually forming tube structures resembling capillaries. VEGFs may cause a massive signaling cascade in endothelial cells. Binding to VEGF2 starts a tyrosine kinase signaling cascade that stimulates the production of factors that variously stimulate vessel permeability, proliferation/survival, migration, and finally differentiation into mature blood vessels. Mechanically, VEGF is upregulated with muscle contractions as a result of increased blood flow to affected areas. The increased flow also causes a large increase in the mRNA production of VEGF receptors 1 and 2. The increase in receptor production indicates that muscle contractions could cause upregulation of the signaling cascade relating to angiogenesis.

In one aspect, provided herein are methods of treating and/or preventing a disease associated with abnormal angiogenesis in a subject in need thereof. In certain embodiments, the disease being treated and/or prevented by the disclosed methods is associated with excessive and/or pathological angiogenesis.

In another aspect, provided herein are methods of treating and/or preventing a disease associated with aberrant signaling of a growth factor in a subject in need thereof. In certain embodiments, the disease is associated with excessive signaling of the growth factor. In certain embodiments, the disease being treated and/or prevented by the disclosed methods is associated with aberrant signaling of VEGF. In certain embodiments, the disease is associated with excessive or aberrant signaling of VEGF-A, VEGF-B, VEGF-C, VEGF-D, VEGF-F, and/or platelet-derived growth factor (PDGF).

In certain embodiments, the disease being treated and/or prevented by the disclosed methods is a proliferative disease. All types of proliferative diseases described herein may be treated and/or prevented by the disclosed methods. In certain embodiments, the disease being treated and/or prevented by the disclosed methods is cancer. All types of cancer described herein may be treated and/or prevented by the disclosed methods. In certain embodiments, the cancer is an ocular cancer. In certain embodiments, the ocular cancer is retinoblastoma, medulloepithelioma, uveal melanoma, ciliary body melanoma, or primary intraocular lymphoma. In certain embodiments, the disease being treated and/or prevented by the disclosed methods is a benign neoplasm. All types of benign neoplasm described herein may be treated and/or prevented by the disclosed methods. In certain embodiments, the benign neoplasm is an ocular benign neoplasm. In certain embodiments, the benign neoplasm is orbital dermoid cysts.

In certain embodiments, the disease being treated and/or prevented by the disclosed methods is an inflammatory disease. All types of inflammatory diseases described herein may be treated and/or prevented by the disclosed methods. In certain embodiments, the inflammatory disease is an ocular inflammatory disease. In certain embodiments, the ocular inflammatory disease is post-surgical inflammation. In certain embodiments, the disease being treated and/or prevented by the disclosed methods is an autoimmune disease. All types of autoimmune diseases described herein may be treated and/or prevented by the disclosed methods. In certain embodiments, the autoimmune disease is rheumatoid arthritis. In certain embodiments, the disease being treated and/or prevented by the disclosed methods is diabetes. In certain embodiments, the disease is type 1 diabetes. In certain embodiments, the disease is type 2 diabetes. In certain embodiments, the disease is gestational diabetes.

In some embodiments the disease being treated and/or prevented by the disclosed methods is an ocular disease. In certain embodiments, the ocular disease is an ocular neovascular disease. In some embodiments, the ocular disease being treated and/or prevented by the disclosed methods is an anterior ocular disease that occurs at the anterior portion or "front" of the eye of a subject. The anterior portion of the eye includes the cornea, iris, conjunctiva, tear film, corneal epithelium, anterior chamber, lens, ciliary body, ciliary zonule, posterior chamber, retina, macula, sclera, an optic nerve, choroid, and vitreous chamber. In certain embodiments, the anterior ocular disease being treated and/or prevented by the disclosed methods is allergy, post-surgical inflammation, uveitis, an infection (e.g., a viral, bacterial, or fungal infection), aphakia, pseudophakia, astigmatism, blepharospasm, cataract, a conjunctival disease, conjunctivitis, a corneal disease, corneal oedema, meibomiam gland disease, corneal transplant surgery, corneal ulcer, dry eye (e.g., dry eye syndrome), an eyelid disease, a lacrimal apparatus disease, lacrimal duct obstruction, laser induced exudation, myopia, presbyopia, pterygium, pupil disorders, corneal neovascularization, a refractive disorder, strabismus, or glaucoma.

In some embodiments, the ocular disease being treated and/or prevented by the disclosed methods is a posterior ocular disease that occurs at the posterior portion or "back" of the eye. The posterior portion of the eye includes the choroid, sclera, vitreous humor, vitreous chamber, retina, macula, optic nerve, and blood vessels and nerves which vascularize or innervate a posterior ocular region or site. In certain embodiments, the posterior ocular disease being treated and/or prevented by the disclosed methods is intraocular melanoma, acute macular neuroretinopathy, an exudative eye disease, Behcet's disease, exudative retinopathy, macular oedema, retinopathy of prematurity, an epiretmal membrane disorder, choroidal neovascularization, uveitis, diabetic uveitis, histoplasmosis, an infection (e.g., a viral, bacterial, or fungal infection), macular degeneration (e.g., acute macular degeneration and age-related macular degeneration (AMD, such as non-exudative age-related macular degeneration and exudative age-related macular degeneration)), edema (e.g., macular edema, such as cystoid macular edema (CME) and diabetic macular edema (DME)), multifocal choroiditis, ocular trauma which affects a posterior ocular site or location, ocular cancer, a retinal disorder (e.g., central retinal vein occlusion), diabetic retinopathy (e.g., proliferative diabetic retinopathy and non-proliferative diabetic retinopathy), proliferative vitreoretinopathy (PVR), retinal arterial occlusive disease, retinal detachment, uveitic retinal disease, sympathetic opthalmia, Vogt Koyanagi-Harada (VKH) syndrome, uveal diffusion, a posterior ocular condition caused by or influenced by an ocular laser treatment, a posterior ocular condition caused by or influenced by a photodynamic therapy, photocoagulation, radiation retinopathy, an epiretinal membrane disorder, branch retinal vein occlusion, anterior ischemic optic neuropathy, non-retinopathy diabetic retinal dysfunction, retinitis pigmentosa, retinoblastoma, or glaucoma. In certain embodiments, the ocular disease being prevented and/or treated by the disclosed methods is macular degeneration. In certain embodiments, the ocular disease is age-related macular degeneration (AMD). In certain embodiments, the ocular disease is glaucoma. In certain embodiments, the ocular disease is diabetic retinopathy. In certain embodiments, the ocular disease is retinoblastoma. In certain embodiments, the ocular disease is edema. In certain embodiments, the ocular disease is cystoid macular edema (CME). In certain embodiments, the ocular disease is diabetic macular edema (DME). In certain embodiments, the ocular disease is an ocular inflammatory disease. In certain embodiments, the ocular disease is post-surgical inflammation. In certain embodiments, the ocular disease is uveitis (e.g., anterior uveitis, intermediate uveitis, and post uveitis). In certain embodiments, the ocular disease is blepharitis. In certain embodiments, the ocular disease is panuveitis. In certain embodiments, the ocular disease is scleritis. In certain embodiments, the ocular disease is dry eye. In certain embodiments, the ocular disease is Sjögren's syndrome. In certain embodiments, the ocular disease is an eye surgery.

Another aspect of the present disclosure relates to methods of inhibiting the aberrant signaling of a growth factor signaling pathway (e.g., VEGF and/or PDGF) in a subject or cell.

In another aspect, the present disclosure provides methods of inhibiting abnormal or pathological angiogenesis in a subject in need thereof.

In one embodiment, the present disclosure relates to a method of treating an ocular disease comprising administering to a subject in need thereof a therapeutically effective amount of a compound of Formula (I), or 1-(4-(3-amino-[1,2,3]triazolo[1,5-a]pyridin-4-yl)phenyl)-3-(3-chlorophenyl)urea, or a pharmaceutically acceptable salt, solvate, hydrate, polymorph, co-crystal, tautomer, stereoisomer, or prodrug thereof, or a pharmaceutical composition thereof.

In one aspect, the ocular disease is retinopathy. In another embodiment, the ocular disease is age-related macular degeneration (AMD). In another embodiment, the ocular disease is an ocular neovascular disease. In another embodiment, the ocular disease is corneal neovascularization. In yet another embodiment, the ocular disease is diabetic macular edema (DME). In a further embodiment, the ocular disease is cystoid macular edema (CME). In yet another embodiment, the ocular disease is retinal vein occlusion (RVO).

In certain embodiments, the subject described herein is a human. In certain embodiments, the subject is an animal. The animal may be of either sex and may be at any stage of development. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

In certain embodiments, the cell described herein is in vivo. In certain embodiments, the cell is in vitro. In certain embodiments, the cell is ex vitro.

In certain embodiments, the methods of the present disclosure include administering to a subject in need thereof an effective amount of compound of Formula (I), or 1-(4-(3-amino-[1,2,3]triazolo[1,5-a]pyridin-4-yl)phenyl)-3-(3-chlorophenyl)urea, or a pharmaceutically acceptable salt, solvate, hydrate, polymorph, co-crystal, tautomer, stereoisomer, or prodrug thereof, or pharmaceutical compositions thereof, as described herein. In certain embodiments, the methods include contacting a cell with an effective amount of a compound of Formula (I), or a pharmaceutical composition thereof, as described herein.

In another aspect, the present disclosure relates to a compound of Formula (I), or 1-(4-(3-amino-[1,2,3]triazolo[1,5-a]pyridin-4-yl)phenyl)-3-(3-chlorophenyl)urea, or a pharmaceutically acceptable salt, solvate, hydrate, polymorph, co-crystal, tautomer, stereoisomer, or prodrug thereof, or pharmaceutical compositions thereof, for use in the treatment and/or prevention of a disease described herein in a subject in need thereof.

In yet another aspect, the present disclosure provides a compound of Formula (I), or 1-(4-(3-amino-[1,2,3]triazolo[1,5-a]pyridin-4-yl)phenyl)-3-(3-chlorophenyl)urea, or a pharmaceutically acceptable salt, solvate, hydrate, polymorph, co-crystal, tautomer, stereoisomer, or prodrug thereof, or pharmaceutical compositions thereof, for use in the inhibition of abnormal angiogenesis in a subject in need thereof.

In still another aspect, the present disclosure provides compound of Formula (I), or 1-(4-(3-amino-[1,2,3]triazolo[1,5-a]pyridin-4-yl)phenyl)-3-(3-chlorophenyl)urea, or a pharmaceutically acceptable salt, solvate, hydrate, polymorph, co-crystal, tautomer, stereoisomer, or prodrug thereof, or pharmaceutical compositions thereof, for use in the inhibition of aberrant signaling of a growth factor in a subject or cell in need thereof.

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Preparation of Intermediate Compound 8

Scheme 1: Synthesis of Intermediate Compound 8.

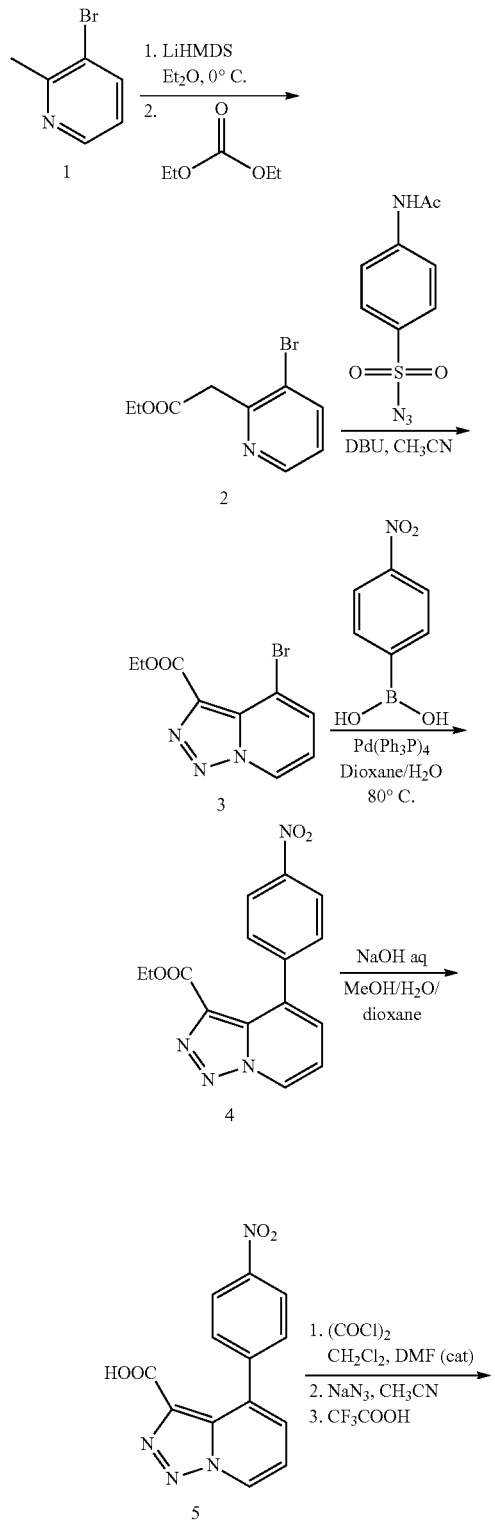

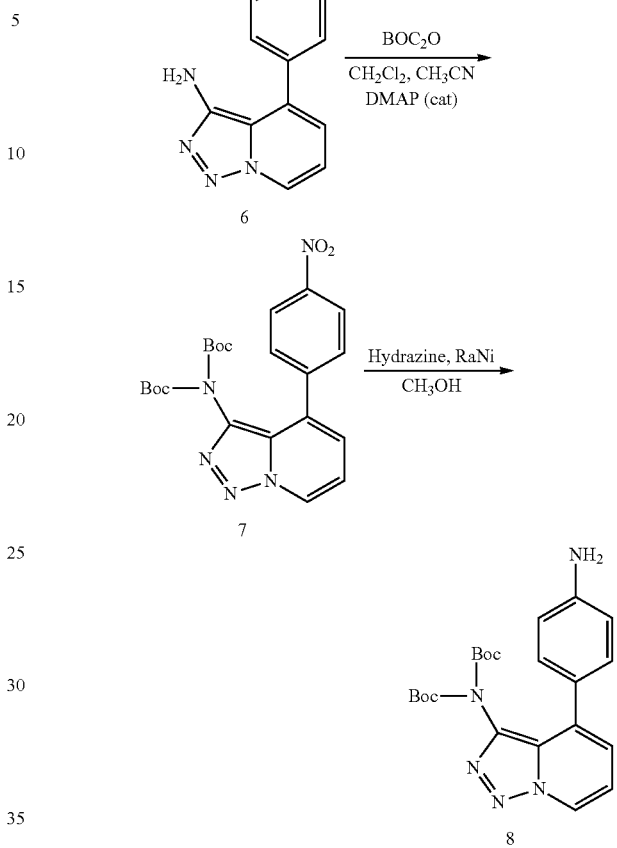

Compound 2

Lithium hexamethyldisilazane (436 mL, 0.44 mmol, 1 M solution in hexanes) was dissolved in diethyl ether (1 L). Compound 1, 3-bromo-2-methylpyridine, (25.0 g, 0.14 mmol) was added. The solution was stirred for 1 h. Diethyl carbonate (26.0 mL, 0.22 mol) was added and the solution was stirred overnight. The reaction solution was washed three times with half-saturated aqueous sodium chloride (3×250 mL) and dried with magnesium sulfate. The solvent was evaporated and the reminder was dissolved in hexanes (200 mL). The solution was filtered through silica pad (10 g), the pad was rinsed with additional hexanes (100 mL) and the solvent was evaporated. The remaining oil was stirred in high vacuum for 1 hour till there were no further bubbles visible. The product was a yellow liquid (37.7 g). LCMS: $[M+H]^+=244.1$.

Compound 3

Compound 2 (37.7 g, 0.15 mol) was dissolved in dry acetonitrile (400 mL). 1,8-diazabicycloundec-7-ene (DBU) (28.2 g, 0.18 mol) was added followed by 4-acetamidobenzenesulfonyl azide (37.6 g, 0.15 mol). The solution was stirred overnight. Water (3 L) was slowly added. The solid was filtered off on a sintered glass funnel and washed with additional water (1 L) and hexanes (0.5 L) and air dried on the fritted funnel for 2 h. The product was a cream solid (27.3 g). LCMS: $[M+H]^+=270.1$.

Compound 4

Compound 3 (10.0 g, 37.0 mmol) and 4-nitrophenylboronic acid (10.0 g, 59.9 mmol) were dissolved in dioxane (150 mL). Sodium carbonate (50 mL, 2 M solution in water) and tetrakistriphenylphosphine (2.0 g, 1.73 mmol) were added. The suspension was degassed by passage of nitrogen (15 min). The solution was heated to 80° C. overnight. Water (500 mL) was added and the precipitate was filtered off, washed with additional portion of water (500 mL) and hexanes (500 mL). The solid was air dried on a sintered glass funnel for 2 hours and then dried in high vacuum overnight. The product was a yellow solid (9.6 g). LCMS: [M+H]+ =313.1.
Compound 5

Compound 4 (9.6 g, 30.8 mmol) was dissolved in a mixture of dioxane (120 mL), methanol (240 mL) and water (240 mL). Sodium hydroxide (42 mL, 10 M in water) was added and the solution was stirred for 6 h. The organic solvents were evaporated. Water (600 mL) was added and the solution was filtered through a CELITE® pad. The filtrate was neutralized with hydrochloric acid (ca. 53 mL, 8 M in water) until the pH was 7. The precipitate was filtered off, washed with water (200 mL) and hexanes (200 mL). The solid was dried in high vacuum overnight. The product was a cream solid (6.8 g). LCMS: [M+H]+=285.1.
Compound 6

Compound 5 (4.7 g, 16.5 mmol) was suspended in dichloromethane (100 mL). Oxalyl chloride (4.2 mL, 49.5 mmol) and N,N-dimethylformamide (50 µL) was added. The suspension was stirred for 1 h at which time all material has dissolved. The solvent was evaporated. The remainder was co-evaporated with dichloromethane (2×100 mL) and dried in high vacuum (30 min). The red solid was dissolved in dry acetonitrile (150 mL). Sodium azide (9.4 g, 14 mmol) was added and the suspension was stirred for 3 h. After this time the LCMS indicated full conversion. Water (1 L) was added and the cream solid was filtered off. The solid was dissolved in trifluoroacetic acid (100 mL). Water (2 mL) was added and the solution was heated at 60° C. for 2 h. After this time LCMS indicated full conversion. The solvent was evaporated and the reminder was dissolved in acetonitrile (50 mL). The acetonitrile solution was slowly added to solution of sodium carbonate (500 mL, 2 M solution in water). The red precipitate was filtered off, washed with additional water (100 mL) and hexanes (100 mL). The solid was air dried on a sintered glass funnel for 2 hours and further dried in high vacuum for 3 h at 45° C. The product was a red solid (3.3 g). LCMS: [M+H]+=256.1. $^1$H NMR (DMSO-d6): 8.78 (d, J=8.5 Hz, 1H), 8.34 (d, J=9.0 Hz, 2H), 8.07 (d, J=8.5 Hz, 1H), 7.72 (d, J=9.0 Hz, 2H), 7.08-7.02 (m, 1H), 4.57 (s, 2H).
Compound 7

Compound 6 (2.6 g, 10.1 mmol) was suspended in dichloromethane (40 mL) and acetonitrile (80 mL). Di-tert-butyl dicarbonate (5.6 g, 25.7 mmol) was added followed up by 4-dimethylaminopyridine (121 mg, 1.0 mmol). The suspension was stirred overnight at which point all the solids have dissolved. The brown solution was evaporated. The residue was co evaporated with dichloromethane (50 mL). The residue was dissolved in dichloromethane (10 mL). Diethyl ether (300 mL) was added and the solution was evaporated (to ca 50 mL). The solution was sonicated and hexanes (100 mL) were added. The precipitate was filtered off and dried in high vacuum for 2 h. The product was a yellow solid (4.0 g). LCMS: [M+Na]+=478.2.
Compound 8

Compound 7 (3.5 g, 7.69 mmol) was dissolved in methanol (250 mL). Raney Nickel (ca. 1 mL, Aldrich, RaNi 2800) was added followed by hydrazine hydrate (2.0 mL, 41.2 mmol). The solution was brought to a brief reflux. When the reflux stopped the LCMS indicated completion of the reaction. The catalyst was filtered off on a CELITE pad. The solvent was evaporated to ca. 10 mL and the residue was diluted with water (200 mL). The solids were filtered off and the residue was washed with water (100 mL) and hexanes (50 mL). The solid was dried in high vacuum overnight. The product was a cream solid (3.0 g). LCMS: [M+H]+=426.3. $^1$H NMR (DMSO-d6): 8.61 (d, J=7.0 Hz, 1H), 7.28-7.25 (m, 2H), 7.13 (d, J=7.0 Hz, 1H), 7.02 (dd, J=7.0, 7.0 Hz, 1H), 6.70 (d, J=9.0 Hz, 2H), 3.85 (s, 2H), 1.31 (s, 18H).

Example 2

Synthesis of 1-(4-(3-amino-[1,2,3]triazolo[1,5-a]pyridin-4-yl)phenyl)-3-(3-chlorophenyl)urea Scheme 2: Synthesis of Compound of Formula (I).

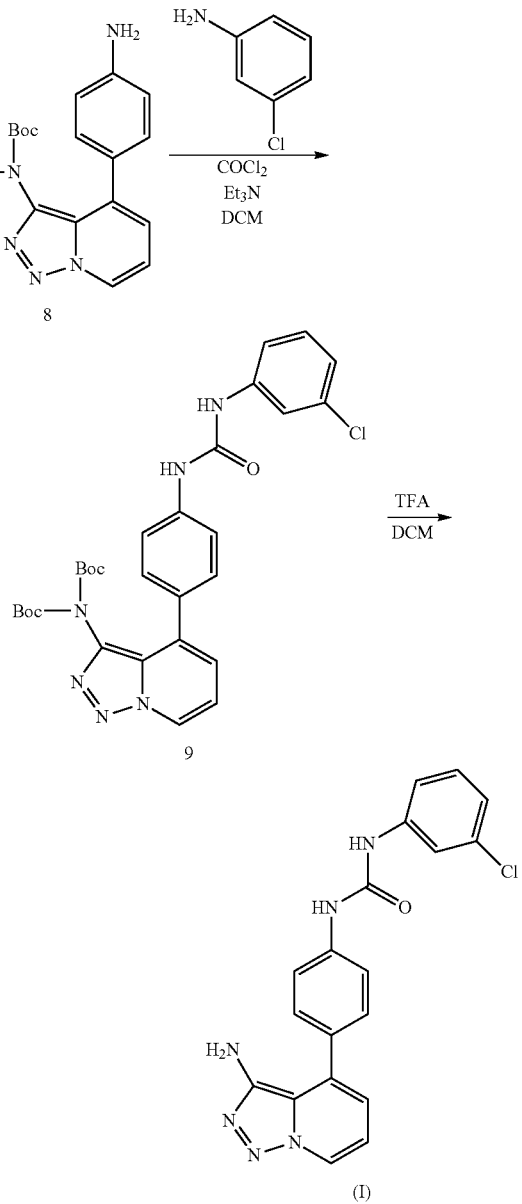

Compound 8, 4-(4-Aminophenyl)-[1,2,3]triazolo[1,5-a]pyridin-3-yl-bis(tert-butyl carbamate) (200 mg, 0.48 mmol)

was dissolved in dichloromethane (20 mL). Triethylamine (0.28 mL, 1.92 mmol) was added, the solution was cooled to −78° C. and phosgene (0.40 mL, 15% solution in toluene, 0.58 mmol) was added. The solution was stirred for 0.5 h and warmed up to room temperature. After 0.5 h 3-chloroaniline (185 mg, 1.46 mmol) was added. The solution was stirred for 2 h. The solvent was evaporated and the residue was purified using flash chromatography (ISCO, 4 g column, 12 column volumes, gradient from dichloromethane to ethyl acetate). The product was a white solid (195 mg). LCMS: 7.54 min, 578.4 (M+, 40%), 577.3 (M-1, 100%) (negative ionization mode).

The material from the previous step (195 mg, 0.34 mmol) was dissolved in dichloromethane (0.5 mL). Trifluoroacetic acid (2 mL) was added and the solution was stirred for 25 min. The solvent was evaporated (at room temperature). The residue was dissolved in dichloromethane (5 mL) and again evaporated. The residue was dissolved in ethyl acetate (20 mL) and the solution was washed with aqueous sodium bicarbonate. The solution was dried with magnesium sulfate and the solvent was evaporated to produce Compound of Formula (I) (112 mg). LCMS: 6.42 min, 380.2 (M+2, 10%), 379.2 (M+1, 30%), 157.1 (100%) (positive ionization mode). $^1$H NMR (dmso-d6): 9.00 (d, J=3.1 Hz, 2H), 8.67 (d, J=7.1 Hz, 1H), 7.75-7.72 (m, 1H), 7.62-7.67 (m, 2H), 7.44-7.51 (m, 2H), 7.29-2.37 (m, 2H), 7.01-7.09 (m, 1H), 6.97 (dd, J=6.4, 24.6 Hz, 2H), 4.45 (s, 2H).

Example 3

Crystalline Form of Compound I

Preparation of Crystalline Form I

Crystal form I was prepared by stirring a slurry of compound I in ethyl acetate.

In one instance, 30.56 mg of compound I was deposited into a 4 mL scintillation vial with screw-top, henceforth referred to as the working vial. To the working vial was added a 12×4.5 mm magnetic stir bar along with 1 mL room temperature ethyl acetate. The vial was capped and transferred into an IKA stirring plate equipped with a magnetic stirrer that was set at room temperature. The suspension in the vial was allowed to stir at room temperature and 500 rpm for 5 days.

After 5 days stirring at room temperature, the solid material was collected by centrifuge filtration and the filtrate was discarded. The centrifuge filter tube was lightly covered then dried under high vacuum for approximately 17 hours. The recovered dried solid was analyzed by XRPD, which showed a unique powder pattern that was assigned as crystal form I.

In another instance, 30.55 mg of compound I was deposited into a 4 mL scintillation vial with screw-top, henceforth referred to as the working vial. To the working vial was added a 12×4.5 mm magnetic stir bar along with 1 mL room temperature ethyl acetate. The vial was capped and transferred into a hot plate equipped with a magnetic stirrer that was preheated to 60° C. The suspension in the vial was allowed to stir at 60° C. and 500 rpm for 5 days.

After 5 days stirring on hot plate, the solid material was collected by centrifuge filtration and the filtrate was discarded. The centrifuge filter tube was lightly covered then dried under high vacuum for approximately 17 hours. The recovered dried solid was analyzed by XRPD, which showed the powder pattern of crystal form I.

Properties of Crystalline Form I

For XRPD, patterns were obtained using a Rigaku MiniFlex 600 benchtop x-ray diffractometer equipped with a Cu X-ray tube (Cu/Kα=1.54059 Å), a six-position sample changer and a D/teX Ultra detector.

Sample Preparation of Neat Crystalline Form for XRPD, Procedure A

As described herein for the characterization of neat crystal Form I, milligram amounts of solid sample were firmly packed in the 5-mm×0.2-mm depression of a zero background sample holder (Rigaku 906166 5 mm×0.2 mm Well, Si510).

Sample Preparation of Milled Crystals for XRPD, Procedure B

As described herein for the characterization of milled crystal form I, particles were isolated from bulk formulation by centrifugation at 55,000 rpm over 15 minutes and deposited thinly and evenly onto a flat zero background XRPD sample holder (Rigaku 906165 Flush, Si510). The sample was allowed to dry under gentle air stream, usually for up to 3 minutes, until it was visually dry.

XRPD patterns were acquired from 3-40° two theta at 0.02° step size and 5°/min scan speed using the following instrument settings: 40 kV-15 mA X-ray generator, 2.5° Soller Slit, 10 mm HIS, 0.625° Divergence Slit, 8 mm Scatter Slit with Kβ filter, and an open Receiving Slit. Diffraction patterns were viewed and analyzed using PDXL analysis software provided by the instrument manufacturer. Using Procedure A, a reference standard silicon powder (NIST Standard Reference Material 640d) generated a peak at 28.39° two theta.

For DSC, about 2 mg of sample was weighed into a standard aluminum sample pan. The sample pan was loaded into the apparatus (Q1000 Differential Scanning Calorimeter, TA Instruments), which was equipped with an autosampler. A thermogram was obtained by individually heating the sample at a rate of 10° C./min from room temperature to approximately 250-300° C. using an empty standard aluminum pan as a reference. Dry nitrogen was used as a sample purge gas and was set to flow at 50 mL/min. Thermal transitions were viewed and analyzed using the analysis software provided with the instrument.

For TGA, about 3 mg of the sample was transferred into an aluminum sample pan. The pan was placed in the loading platform and was then automatically loaded into the apparatus (Q500 Thermogravimetric Analyzer, TA Instruments) using the control software. Thermograms were obtained by individually heating the sample at 10° C./min from room temperature to 300° C. under flowing dry nitrogen, with a sample purge flow rate of 25 mL/min and a balance purge flow rate of 10 mL/min. Thermal transitions (e.g., weight changes) were viewed and analyzed using the analysis software provided with the instrument.

The XRPD pattern of crystal form I is illustrated in FIG. 1. A tabulation of the peaks in two-theta and the corresponding d-spacing values comprised in the XRPD patter of form I are listed in Table 1.

TABLE 1

| | XRPD peak listing of neat crystal form I | | |
|---|---|---|---|
| Peak No. | Position ± 0.2° [2θ] | d-spacing ± 0.2 [Å] | Relative Intensity [%] |
| 1 | 8.05 | 10.98 | 4.96 |
| 2 | 10.54 | 8.39 | 15.44 |

TABLE 1-continued

XRPD peak listing of neat crystal form I

| Peak No. | Position ± 0.2° [2θ] | d-spacing ± 0.2 [Å] | Relative Intensity [%] |
|---|---|---|---|
| 3 | 11.53 | 7.67 | 1.86 |
| 4 | 12.24 | 7.22 | 4.43 |
| 5 | 14.36 | 6.16 | 35.85 |
| 6 | 14.83 | 5.97 | 9.77 |
| 7 | 15.82 | 5.60 | 12.44 |
| 8 | 16.16 | 5.48 | 20.38 |
| 9 | 16.48 | 5.37 | 3.20 |
| 10 | 17.16 | 5.16 | 4.98 |
| 11 | 19.26 | 4.60 | 17.00 |
| 12 | 20.20 | 4.39 | 23.68 |
| 13 | 20.56 | 4.32 | 5.67 |
| 14 | 21.28 | 4.17 | 6.86 |
| 15 | 21.67 | 4.10 | 40.30 |
| 16 | 22.46 | 3.95 | 2.720 |
| 17 | 23.13 | 3.84 | 3.32 |
| 18 | 24.06 | 3.70 | 10.18 |
| 19 | 24.72 | 3.60 | 100.00 |
| 20 | 25.27 | 3.52 | 26.26 |
| 21 | 25.99 | 3.43 | 26.22 |
| 22 | 26.23 | 3.40 | 52.39 |
| 23 | 26.77 | 3.33 | 13.18 |
| 24 | 27.64 | 3.22 | 4.30 |
| 25 | 28.96 | 3.08 | 19.91 |
| 26 | 29.44 | 3.03 | 12.11 |
| 27 | 30.36 | 2.94 | 12.86 |
| 28 | 31.23 | 2.86 | 8.09 |
| 29 | 32.43 | 2.76 | 8.69 |
| 30 | 34.02 | 2.63 | 3.27 |
| 31 | 34.92 | 2.57 | 6.67 |
| 32 | 35.88 | 2.50 | 5.59 |

Figure 2:
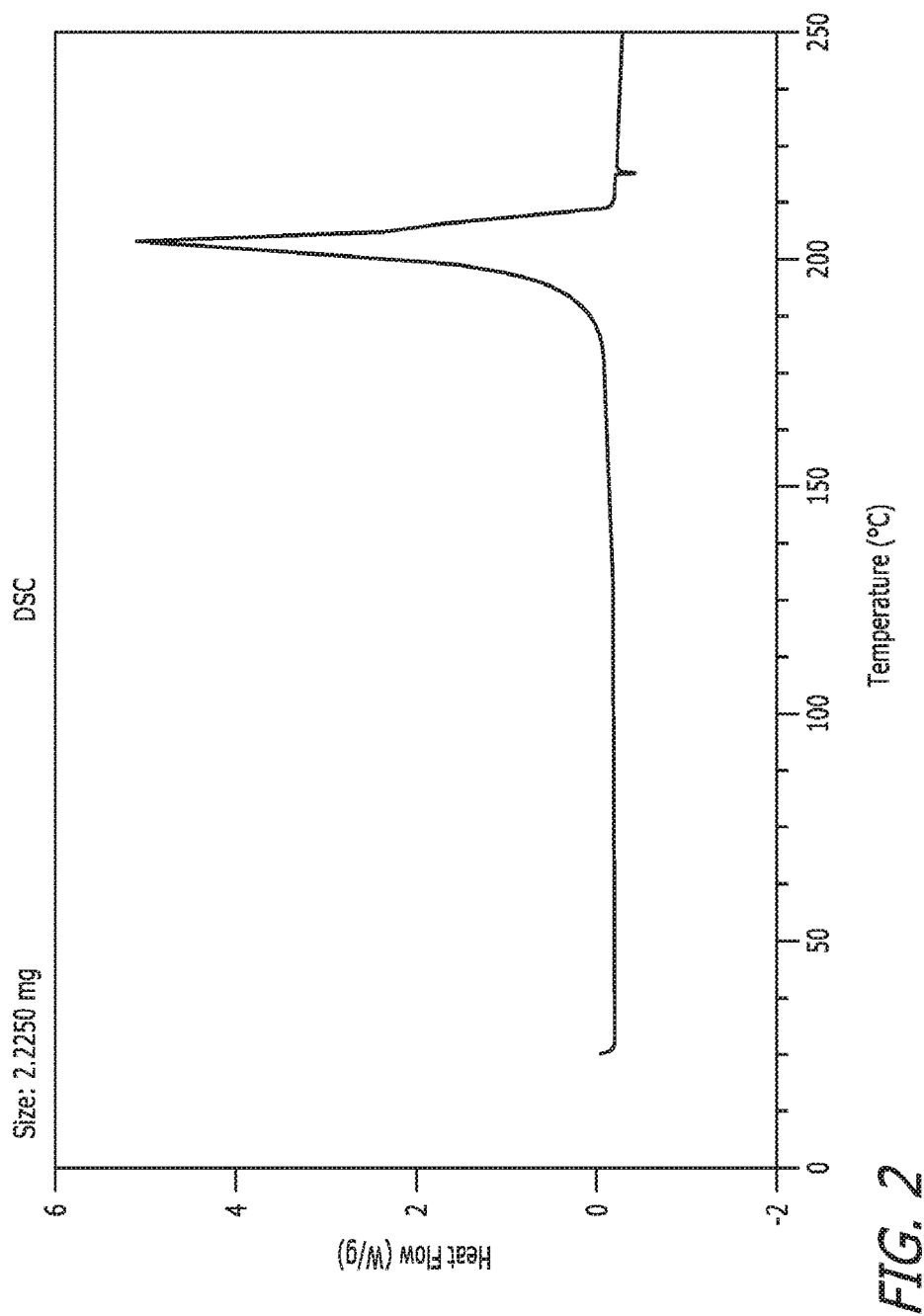
FIG. 2 depicts a differential scanning calorimetry (DSC) thermogram of crystal form I of Compound I.
Figure 3:
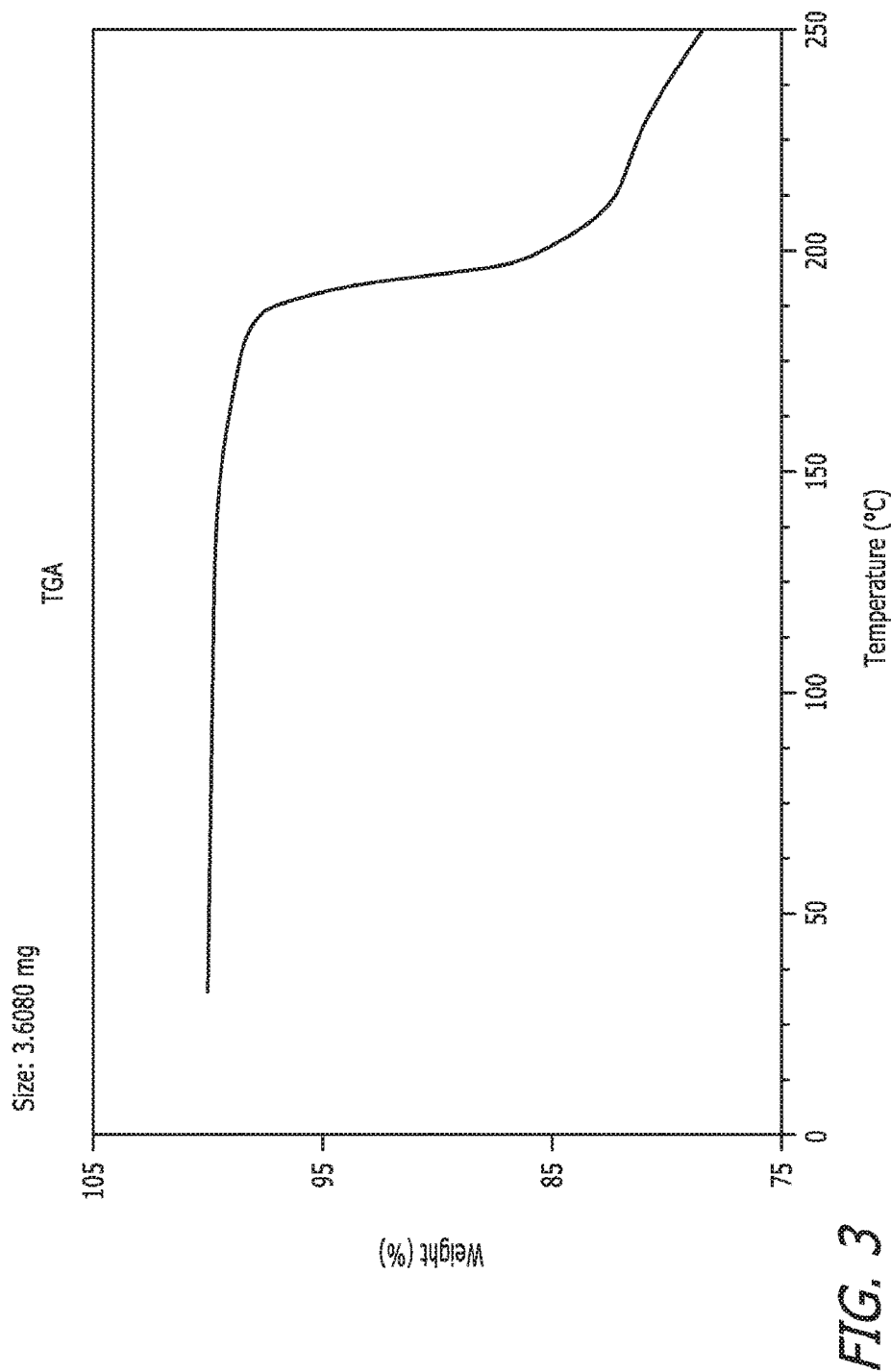
FIG. 3 depicts a thermal gravim analysis (TGA) thermogram of crystal form I of Compound I.

FIG. 2 shows that the DSC thermogram measured from 25° C. to 300° C., ramped at 10° C./min, was found to decompose without melting beyond 170° C. FIG. 3 shows that the TGA thermogram measured from 25° C. to 300° C., ramped at 10° C./min, was also found to decomposes above 170° C. The DSC and TGA thermograms both indicate that crystal form I is an anhydrate form that decomposes above 170° C.

Example 4

Mucus Penetrating Particles (MPP) of Crystal Form I of Compound I

A wet milling process was employed to generate MPP. Milling media, specifically 0.5 mL bulk volume of 1-mm ceria-stabilized zirconium oxide beads, was added to a glass vial. Approximately 25 mg of Compound I and 0.475 mL of milling solution, 5% (final w/w) PLURONIC® F127 in PBS (0.0067 M ($PO_4^{3-}$) phosphate buffered saline pH 7.2), were then added to the vial yielding a slurry of 5% Compound I (w/v). A magnetic stir bar was used to agitate the beads, stirring at approximately 500 rpm. Particle size after milling is listed in Table 2.

TABLE 2

Examples of formulating MPP of Compound I crystal form I.

| Starting Form | Milling Time (days) | Particle Size (nm) | MPP Form |
|---|---|---|---|
| crystal form I | 3 | 190 | crystal form I |

Figure 4:
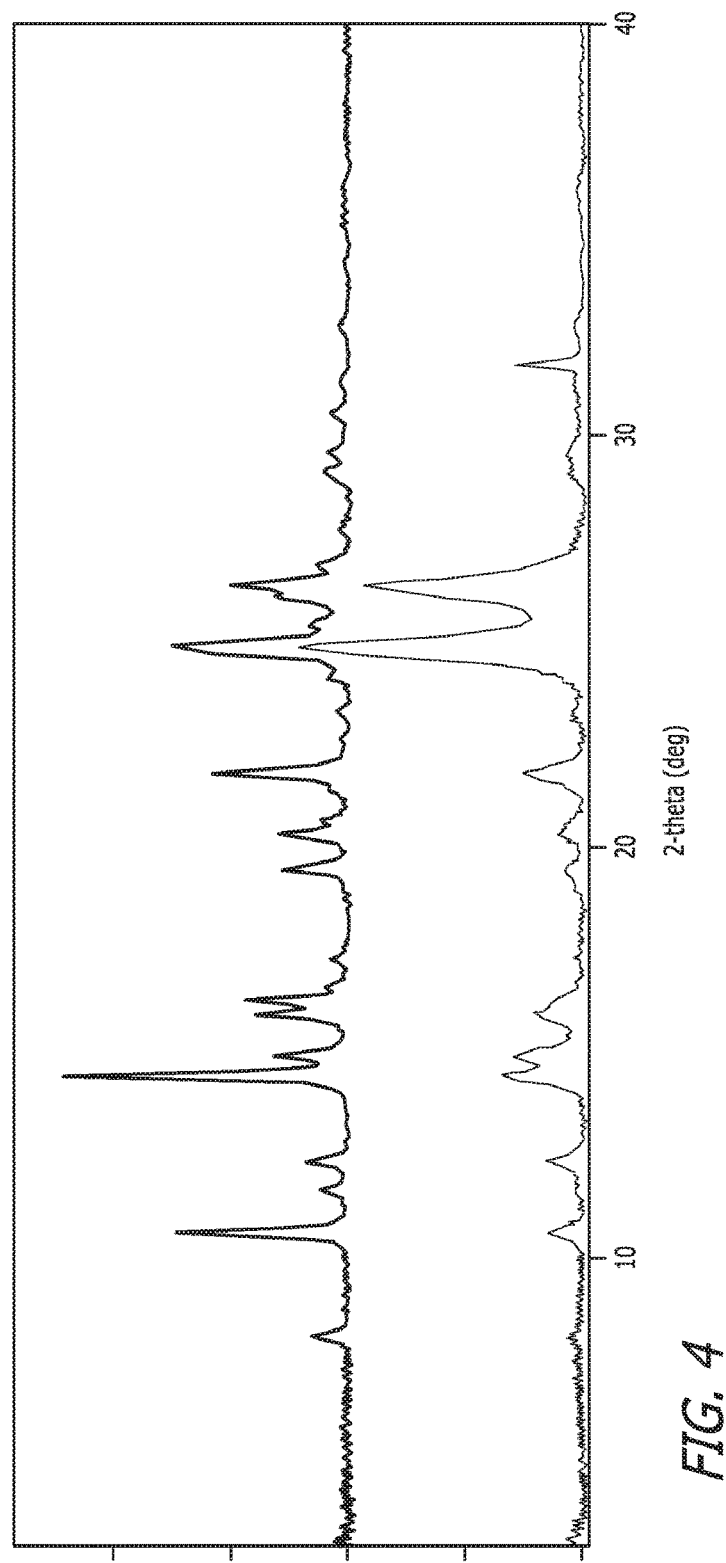
FIG. 4 depicts the XRPD pattern of crystal form I after milling.

After milling, XRPD patterns of Compound I with excipients still present were collected using Procedure B. Neat crystal form I is stable when formulated as an MPP; details are listed in Table 2. FIG. 4 shows XRPD patterns, which demonstrate that the crystalline form was unchanged after milling.

Example 5

Cellular Assays: Vascular Endothelial Growth Factor Receptor 2 (VEGFR2) and Platelet-Derived Growth Factor Receptor-β (PDGFR-β)

The human umbilical endothelial (HUE) cell line expresses high levels of VEGFR2. The compound prepared in Example 2 above, 1-(4-(3-amino-[1,2,3]triazolo[1,5-a]pyridin-4-yl)phenyl)-3-(3-chlorophenyl)urea, was tested for the ability to inhibit tyrosine auto-phosphorylation of this receptor after stimulation with vascular endothelial growth factor A (VEGF-A). HUE cells were plated into multi-well cell culture plates in endothelial cell growth medium (ECGM) supplemented with 10% fetal calf serum (FCS). After starvation in endothelial cell basal medium (ECBM) supplemented with 10% FCS overnight cells were incubated with compounds in serum-free ECBM. On the day of the assay the medium was changed to serum-free ECBM, the compound was 1:3 serial diluted from 10 mM stock in 100% DMSO and then 1:100 diluted to each well of cells in ECBM without FCS to create final solutions containing 1% DMSO and an eight point compound close response curve starting at $10^{-7}$ M, $10^{-8}$ M, or $10^{-9}$ M. The compound was added in duplicate to the multi-well cell culture plate. For controls, cells in one column of wells were treated with 1% DMSO to serve as High Control, and a second column of wells was treated with $10^{-5}$ M staurosporine to serve as Low Control for the assay. Cells were incubated for 90 min at 37° C. in ECBM with the serial diluted compound and then stimulated for 3 min with 100 ng/ml VEGF-A. Cells were lysed, and then levels of phosphorylated VEGFR2 were determined in a sandwich ELISA assay formatted in a multi-well plate using a VEGFR2 specific capture antibody and an anti-phosphotyrosine VEGFR2 detection antibody. The raw data were converted to percent tyrosine phosphorylated VEGFR2 with respect to the on plate High and Low Controls. $IC_{50}$ values were determined by fitting the converted eight point close response data to a four-parameter logistic equation using GRAPHPAD PRISM® 5.01 software.

The murine embryonal fibroblast cell line NIH3T3 expresses endogenously high levels of PDGFR-β. The compound prepared in Example 2 above was tested for the ability to inhibit tyrosine auto-phosphorylation of this receptor after stimulation with platelet-derived growth factor BB (PDGF-BB). The NIH3T3 cells were plated into multi-well cell culture plates in Dulbecco's Modified Eagle Medium (DMEM) supplemented with 10% FCS. The medium was removed and then replaced with DMEM without FCS and cells serum starved overnight at 37° C. On the day of the assay the compound was 1:3 serial diluted from 10 mM stocks in 100% DMSO and then were 1:100 diluted to each well of cells in DMEM without FCS to create final solutions containing 1% DMSO and an eight point compound close response curve starting at $10^{-6}$ M, $10^{-7}$ M, or $10^{-8}$ M. The compound was added in duplicate to columns of the multi-well plate. Cells in one column of wells of the multi-well plate were treated with 1% DMSO to serve as High Control, and cells in a second column of wells were treated with $10^{-5}$ M staurosporine to serve as Low Control for the assay. Cells were incubated for 90 min at 37° C. in DMEM with the serial diluted compound and then stimulated for 3 min with 100 ng/ml PDGF-BB. Cells were lysed, and then levels of phosphorylated PDGFR-β were determined in a sandwich ELISA assay formatted in a multi-well plate using a PDGFR-β specific capture antibody and an anti-phosphotyrosine PDGFR-β detection antibody. The raw data were converted to percent phosphorylated PDGFR-β with respect to the on plate High and Low Controls. $IC_{50}$ values were determined by fitting the converted eight point close response data to a four-parameter logistic equation using GRAPHPAD PRISM® 5.01 software.

The results of these cellular assays indicated that the compound of Formula (I) is a potent inhibitor of VEGFR2 and PDGFR-1 with cellular $IC_{50}$ values of 0.37 nM and 3.2 nM, respectively.

Example 6

Pharmacokinetic (PK) Study in Pigs

A pharmacokinetic (PK) study of a compound of Formula (I) formulated as a mucus-penetrating particles or nanocrystals (MPP) is performed in order to demonstrate topical instillation results in drug exposure at the back of the eye.

For example, pigs (such as Gottingen mini-pigs or Sinclair pigs) are used to perform a PK study. Animals receive a single topical ocular close (e.g., a close volume of 35 μL) in the right eye twice daily (BID), approximately 12 hr apart (±1 hour), for 4 consecutive days; on the fifth day animals will receive a single topical ocular close in the morning only for a total of 9 closes over the study duration.

All animals are euthanized with sodium pentobarbital and blood is collected via cardiac puncture into tubes containing $K_2EDTA$, which is centrifuged to obtain plasma. Then, both eyes are enucleated, flash frozen and stored at −70° C. for at least 2 hr. Within approximately 2 days, the frozen matrices are collected as right and left eye for choroid and retina. Drug exposures in plasma and back of the eye are then determined.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

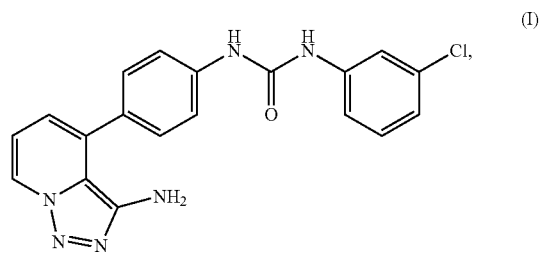 [SMILES: Nc1nnn2cccc(-c3ccc(NC(=O)Nc4cccc(Cl)c4)cc3)c12]

or a pharmaceutically acceptable salt thereof.

2. A crystal form of

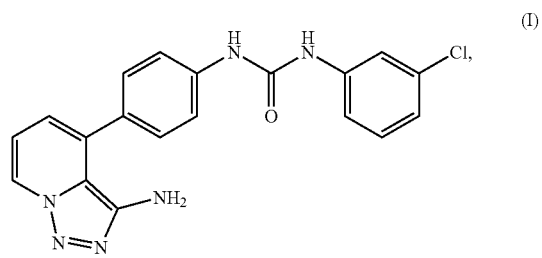 [SMILES: Nc1nnn2cccc(-c3ccc(NC(=O)Nc4cccc(Cl)c4)cc3)c12]

wherein the crystal form has an X-ray powder diffraction (XRPD) pattern with peaks at about 10.5, about 14.4, about 19.3, about 21.7, and about 24.7 degrees 2θ.

3. A pharmaceutical composition comprising a compound of claim 1, or a pharmaceutically acceptable salt thereof, or a crystal form of claim 2, and a pharmaceutically acceptable excipient or carrier.

4. The pharmaceutical composition of claim 3, wherein the pharmaceutical composition is suitable for topical administration, injection, oral administration, or inhalation.

5. The pharmaceutical composition of claim 3, wherein the pharmaceutical composition is suitable for delivery to the eye.

6. The pharmaceutical composition of claim 5, wherein the pharmaceutical composition is in a container configured to administer eye drops.

7. A method of inhibiting growth factor signaling comprising administering to a subject in need thereof a therapeutically effective amount of a pharmaceutical composition of claim 3.

8. The method according to claim 7, wherein the pharmaceutical composition is administered topically, by injection, orally, or by inhalation.

9. The method according to claim 7, wherein the pharmaceutical composition is administered to the eye.

* * * * *